(12) United States Patent
Wang

(10) Patent No.: US 7,455,658 B2
(45) Date of Patent: Nov. 25, 2008

(54) FLUID DISPENSING OR FEEDING DEVICE

(76) Inventor: Samw Hong Jen Wang, No. 14-3, Fusing 1st Road, Sinsing District, Kaohsiung Hsien 800053 (TW)

(*) Notice: Subject to any disclaimer, the term of this patent is extended or adjusted under 35 U.S.C. 154(b) by 471 days.

(21) Appl. No.: 10/986,416

(22) Filed: Nov. 10, 2004

(65) Prior Publication Data
US 2006/0249541 A1    Nov. 9, 2006

(51) Int. Cl.
    *B65D 88/54* (2006.01)
(52) U.S. Cl. .................... 604/85; 604/85; 604/251; 222/386; 222/529
(58) Field of Classification Search ............. 222/333, 222/386, 529; 604/85, 251
    See application file for complete search history.

(56) References Cited

U.S. PATENT DOCUMENTS 2,850,211 A    9/1958  Fernandez
3,227,173 A    1/1966  Bernstein
4,243,032 A *  1/1981  Howell ................. 604/251
5,014,884 A *  5/1991  Wunsch ................. 222/333
5,295,890 A *  3/1994  Myers .................. 446/176
5,316,186 A *  5/1994  Prestele ............... 222/386
2004/0182887 A1* 9/2004 Sugimura et al. ........ 222/386

* cited by examiner

Primary Examiner—Frederick C. Nicolas
(74) Attorney, Agent, or Firm—Charles E. Baxley

(57) ABSTRACT

A fluid dispensing device includes a bottle for receiving fluid, a discharge tube, and a pressurizing device coupled between the bottle and the discharge tube, for pressurizing the fluid and for forcing the fluid to flow through the discharge tube without gravity. The pressurizing device includes a container coupled between the bottle and the discharge tube, a piston slidably received in the container, and a moving device for moving the piston in a reciprocating action within the container. For example, a motor is coupled to the piston with a crank, to move the piston in the reciprocating action within the container.

7 Claims, 2 Drawing Sheets

FLUID DISPENSING OR FEEDING DEVICE

BACKGROUND OF THE INVENTION

1. Field of the Invention

The present invention relates to a fluid dispensing or feeding device, and more particularly to a fluid dispensing or feeding device having a pressurizing device for pressurizing fluid and for allowing fluid bottle to be disposed below hearts of patients or users, and thus for allowing the fluid dispensing or feeding device to be easily carried by the patients or users.

2. Description of the Prior Art

Typically, fluid dispensing or feeding devices have been developed and provided for feeding or injecting medicinal fluids intravenously into human body tissue, and comprise a feed tube having a hypodermic needle provided on one end thereof for engaging into a fluid bottle or container, and having an injection needle provided on the other end thereof, for penetrating into patient's body tissue and for the purposes of injecting the fluid as desired.

The flow of fluid from the bottle is normally by gravity and is regulated by a clamp valve on the flexible outlet tube so as to control the dispensing of the fluid. Also positioned in the discharge line and located near the bottle is a drip meter or flow indicating device usually made of transparent material for allowing the drops of fluid passing from the bottle to the tubes may be observed.

For example, U.S. Pat. No. 2,850,211 to Fernandez, and U.S. Pat. No. 3,227,173 to Bernstein disclose two of the typical fluid dispensing or feeding devices, which also include a bottle or container for receiving fluid therein, and arranged for allowing the fluid to flow into patient's body tissue by gravity, and which comprise safety valves for limiting the flow of the fluid, and for preventing the fluid from flowing backward to the bottle.

Normally, the fluid bottle or container is required to be held or supported above the heart of the patient, for allowing the fluid to suitably flow into patient's body tissue by gravity. Once the fluid bottle or container is disposed below the heart of the patient, the fluid may no longer suitably flow into patient's body tissue by gravity.

However, it is inconvenient for the users, particularly the patient to support the fluid bottle or container above the heart of the patient, such that the patients are normally confined or prohibited from going too far from hospitals.

The present invention has arisen to mitigate and/or obviate the afore-described disadvantages of the conventional fluid dispensing or feeding devices.

SUMMARY OF THE INVENTION

The primary objective of the present invention is to provide a fluid dispensing device including a pressurizing device for pressurizing fluid and for allowing fluid bottle to be disposed below hearts of patients or users, and thus for allowing the fluid dispensing or feeding device to be easily carried by the patients or users.

In accordance with one aspect of the invention, there is provided a fluid dispensing device comprising a bottle for receiving fluid therein, a discharge tube, and a pressurizing device attached and coupled between the bottle and the discharge tube, for pressurizing the fluid and for forcing the fluid to flow through the discharge tube without gravity.

The pressurizing device includes a container coupled between the bottle and the discharge tube, a piston slidably received in the container, and a moving device for moving the piston in a reciprocating action within the container.

The piston includes a valve member attached to the piston, to selectively block one or more passages of the piston, and to form a check valve. The valve member is a rubber panel attached to the piston, and located closer to the plug and distal to the cap.

The moving device includes a motor coupled to the piston, to move the piston in the reciprocating action within the container. The motor includes a crank coupled to the spindle and the piston, to move the piston in the reciprocating action by the motor.

The piston includes an extension extended therefrom, and a link coupled between the extension of the piston and the crank, to allow the piston to be moved by the motor via the crank. The moving device includes at least one battery coupled to the motor, to energize the motor.

The discharge tube includes a flow indicating device attached thereto to allow drops of the fluid passing from the bottle to the discharge tube to be observed. The discharge tube may further include a clamp valve attached thereto, to control dispensing and rate of flow of the fluid. The discharge tube may further include an air relief valve attached thereto, to selectively relieve air.

Further objectives and advantages of the present invention will become apparent from a careful reading of the detailed description provided hereinbelow, with appropriate reference to the accompanying drawings.

DETAILED DESCRIPTION OF THE PREFERRED EMBODIMENT

Figure 1:
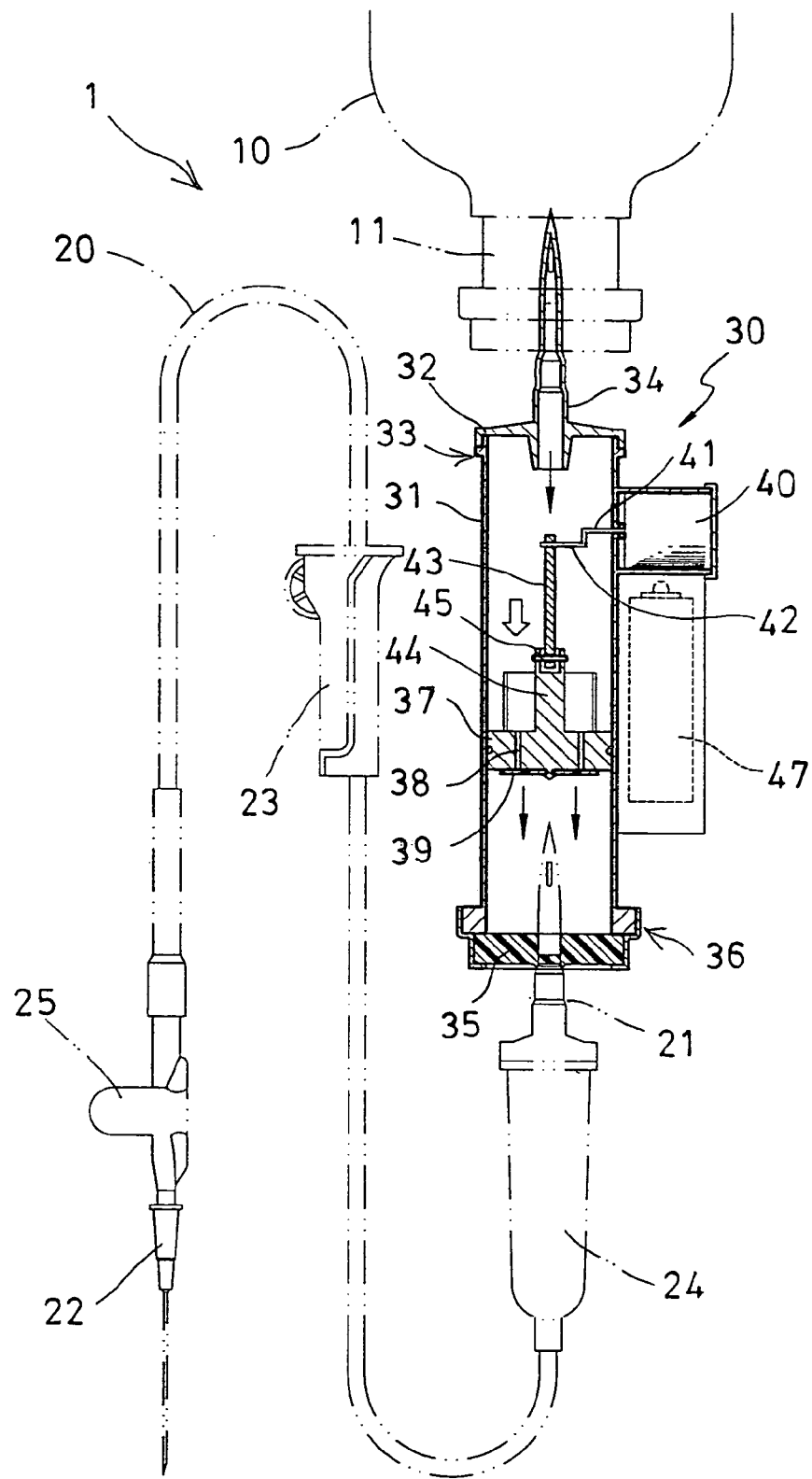
FIG. 1 is a partial cross sectional view of a fluid dispensing device in accordance with the present invention.

Referring to the drawings, and initially to FIG. 1, a fluid dispensing or feeding device 1 in accordance with the present invention comprises a typical fluid container or bottle 10 for receiving fluids, such as medicinal fluids to be fed or injected intravenously into human body tissue, and a typical delivery or discharge tube 20 having a hollow hypodermic needle 21 provided on one end thereof for coupling to the bottle 10, and having an injection needle 22 provided on the other end thereof, for penetrating into patient's body tissue and for the purposes of injecting the fluid as desired.

A clamp valve 23 is attached onto the flexible discharge tube 20 so as to control the dispensing or the rate of flow of the fluid in the well known manner. Also positioned in the discharge tube 20 and located near the hollow hypodermic needle 21 or the bottle 10 is a drip meter or flow indicating device 24 usually made of transparent material for allowing the drops of fluid passing from the bottle 10 to the discharge tube 20 may be observed.

The fluid dispensing or feeding device 1 in accordance with the present invention further comprises a pressurizing device 30 attached to or coupled between the bottle 10 and the discharge tube 20, for pressurizing the fluid and for allowing the fluid to flow through the discharge tube 20 without gravity, and thus for allowing the fluid bottle 10 to be disposed below the hearts of the patients or users, and thus for allowing the fluid dispensing or feeding device 1 to be easily carried by the patients or users.

The pressurizing means or device 30 includes a container 31 having a cap 32 attached to one end or portion 33 thereof, and a hollow hypodermic needle 34 provided on or attached onto or extended from the cap 32, for engaging into the bottle neck portion 11 of the bottle 10, and thus for receiving the fluid from the bottle 10. The container 31 includes a plug 35 attached to the other end or portion 36 thereof, for blocking or enclosing the other end or portion 36 of the container 31. The hollow hypodermic needle 21 of the discharge tube 20 is to be engaged through the plug 35 and into the container 31, for allowing the fluid to flow out of the fluid container 31 and to flow through the discharge tube 20.

The pressurizing device 30 further includes a piston 37 slidably received in the container 31, and having one or more passages 38 formed therein, and a valve member 39 in the form of rubber panel 39 attached to the piston 37 and located closer to the plug 35, but distal to the cap 32, in order to selectively block the passages 38 of the piston 37, and so as to form a check valve, and to allow the piston 37 to force the fluid toward the plug 35 and into the discharge tube 20 via the hollow hypodermic needle 21 when the piston 37 is moved toward the plug 35 or away from the cap 32, and also to allow the fluid to flow through the passages 38 of the piston 37 when the piston 37 is moved away from the plug 35 or toward the cap 32.

A motor 40 is further provided and attached to the container 31, and includes a spindle 41 extended into the container 31, and an eccentric crank 42 coupled to the spindle 41, for allowing the crank 42 to be rotated or driven by the spindle 41 of the motor 40. A link 43 is coupled to an extension 44 of the piston 37 with a pivot pin 45, to allow the piston 37 to be moved or driven in a reciprocating action within the container 31 by the motor 40 via the crank 42. One or more batteries 47 may further be provided and coupled to the motor 40 in order to energize and actuate the motor 40.

In operation, as shown in FIG. 1, when the piston 37 is moved or driven toward the plug 35 or away from the cap 32 by the motor 40, the fluid contained in the lower portion 36 of the container 31 may be forced to flow toward the plug 35 and to flow into the discharge tube 20 via the hollow hypodermic needle 21, such that the fluid may be pressurized by the motor 40 and may be forced to flow through the discharge tube 20 without gravity, such that the fluid bottle 10 may be disposed below the hearts of the patients or users, and thus such that the fluid dispensing or feeding device 1 may be easily carried by the patients or users.

Figure 2:
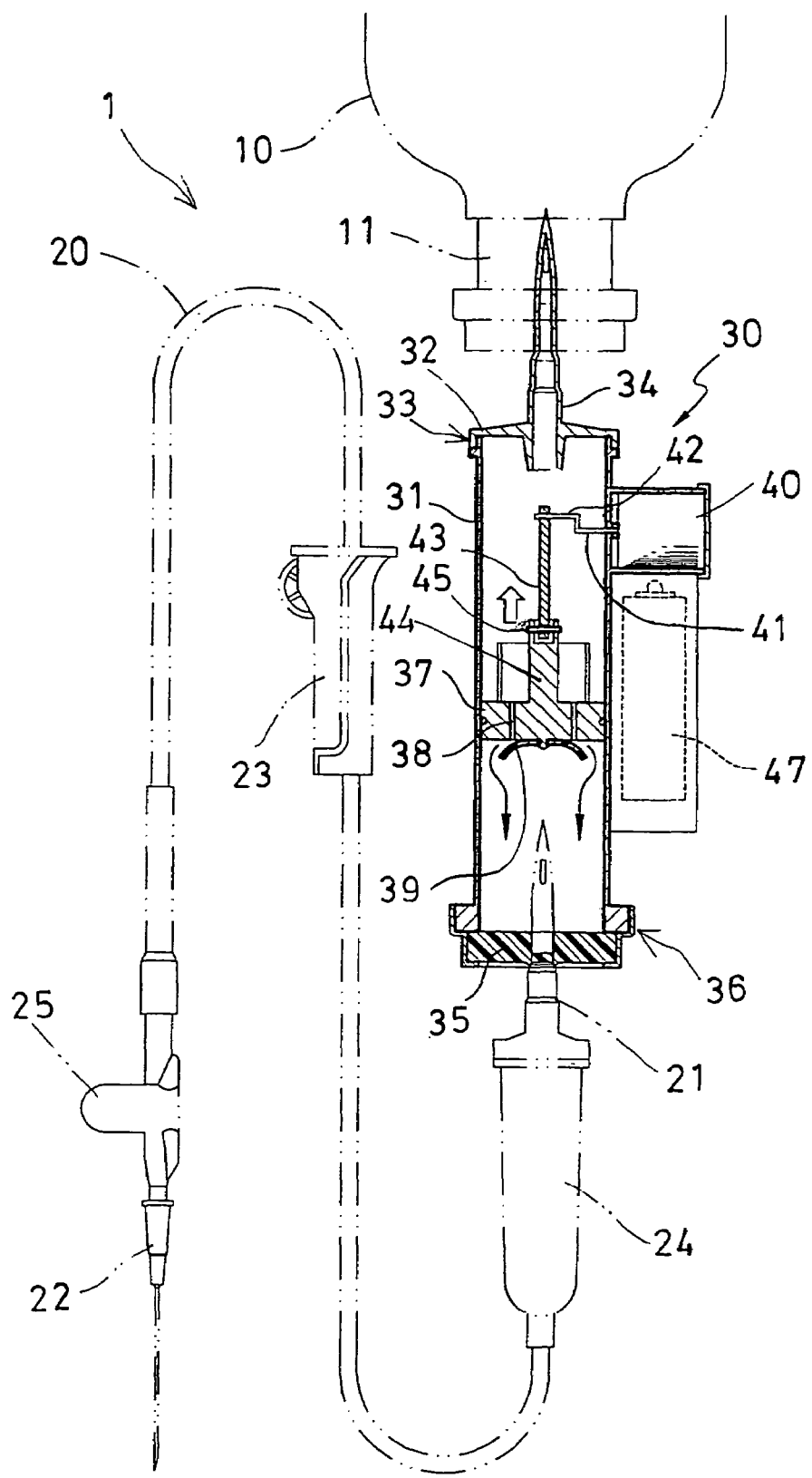
FIG. 2 is a partial cross sectional view of the fluid dispensing device, similar to FIG. 1, illustrating the operation of the fluid dispensing device.

As shown in FIG. 2, when the piston 37 is moved or driven away from the plug 35 or toward the cap 32 by the motor 40, the fluid contained in the upper portion 33 of the container 31 may flow through the passages 38 of the piston 37 and may then flow into the lower portion 36 of the container 31, for being forced to flow into the discharge tube 20 again when the piston 37 is moved or driven toward the plug 35 or away from the cap 32 by the motor 40 again, such that the fluid may be pressurized by the motor 40 in reciprocating action, and may be controlled and forced to flow through the discharge tube 20 without gravity.

The motor 40 and the piston 37 and/or clamp valve 23 and/or the flow indicating device 24 may be suitably arranged to control the dispensing or the rate of flow of the fluid through the discharge tube 20, and to prevent the fluid from being over pressurized. An air relief valve 25 may further be provided and attached to the discharge tube 20, and preferably disposed close to the injection needle 22, for selectively relieving air, and for preventing air from being injected into human body tissue inadvertently, when no fluid is forced to flow through the discharge tube 20. The motor 40 may be controlled or actuated by a switch (not shown) or the like.

Accordingly, the fluid dispensing device in accordance with the present invention includes a pressurizing device for pressurizing fluid and for allowing fluid bottle to be disposed below hearts of patients or users, and thus for allowing the fluid dispensing or feeding device to be easily carried by the patients or users.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

I claim:

1. A fluid dispensing device comprising:
    a bottle for receiving fluid therein,
    a discharge tube, and
    a pressurizing device attached and coupled between said bottle and said discharge tube, for pressurizing the fluid and for forcing the fluid to flow through said discharge tube without gravity, said pressurizing device including a container coupled between said bottle and said discharge tube, a piston slidably received in said container, and means for moving said piston in a reciprocating action within said container, said moving means including a motor coupled to said piston, to move said piston in the reciprocating action within said container, said motor including a spindle, and a crank coupled to said spindle and coupled to said piston, to move said piston in the reciprocating action by said motor, and
    said discharge tube including an air relief valve attached thereto, to selectively relieve air.

2. The fluid dispensing device as claimed in claim 1, wherein said piston includes an extension extended therefrom, and a link coupled between said extension of said piston and said crank, to allow said piston to be moved by said motor via said crank.

3. The fluid dispensing device as claimed in claim 1, wherein said moving means includes at least one battery coupled to said motor, to energize said motor.

4. A fluid dispensing device comprising:
    a bottle for receiving fluid therein,
    a discharge tube, and
    a pressurizing device attached and coupled between said bottle and said discharge tube, for pressurizing the fluid and for forcing the fluid to flow through said discharge tube without gravity, said pressurizing device including a container coupled between said bottle and said discharge tube, a piston slidably received in said container, and means for moving said piston in a reciprocating action within said container, said moving means including a motor coupled to said piston, to move said piston in the reciprocating action within said container, said motor including a spindle, and a crank coupled to said spindle and coupled to said piston, to move said piston in the reciprocating action by said motor, said piston including at least one passage formed therein, and a valve member attached to said piston, to selectively block said passages of said piston, and to form a check valve.

5. The fluid dispensing device as claimed in claim 4, wherein said valve member is in form of rubber panel attached to said piston.

6. A fluid dispensing device comprising:

a bottle for receiving fluid therein, a discharge tube, a pressurizing device attached and coupled between said bottle and said discharge tube, for pressurizing the fluid and for forcing the fluid to flow through said discharge tube without gravity, said pressurizing device including a container coupled between said bottle and said discharge tube, a piston slidably received in said container, and means for moving said piston in a reciprocating action within said container, said moving means including a motor coupled to said piston, to move said piston in the reciprocating action within said container, said motor including a spindle, and a crank coupled to said spindle and coupled to said piston, to move said piston in the reciprocating action by said motor, and said discharge tube including a flow indicating device attached thereto to allow drops of the fluid passing from said bottle to said discharge tube to be observed.

7. A fluid dispensing device comprising:

a bottle for receiving fluid therein, a discharge tube, a pressurizing device attached and coupled between said bottle and said discharge tube, for pressurizing the fluid and for forcing the fluid to flow through said discharge tube without gravity, said pressurizing device including a container coupled between said bottle and said discharge tube, a piston slidably received in said container, and means for moving said piston in a reciprocating action within said container, said moving means including a motor coupled to said piston, to move said piston in the reciprocating action within said container, said motor including a spindle, and a crank coupled to said spindle and coupled to said piston, to move said piston in the reciprocating action by said motor, and said discharge tube including a clamp valve attached thereto, to control dispensing and rate of flow of the fluid.

* * * * *